US008263402B1

(12) United States Patent
Goldman et al.

(10) Patent No.: US 8,263,402 B1
(45) Date of Patent: Sep. 11, 2012

(54) METHOD FOR ISOLATING AND PURIFYING OLIGODENDROCYTES AND OLIGODENDROCYTE PROGENITOR CELLS

(75) Inventors: Steven A. Goldman, South Salem, NY (US); Su Wang, Palisades Park, NJ (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/282,239

(22) Filed: Mar. 31, 1999

Related U.S. Application Data

(60) Provisional application No. 60/104,809, filed on Oct. 19, 1998.

(51) Int. Cl.
  *C12N 5/02* (2006.01)
  *C12N 5/071* (2010.01)
(52) U.S. Cl. .................. 435/368; 435/366; 435/325
(58) Field of Classification Search .............. 424/93.7; 435/6, 325, 240.2, 318, 366, 378
  See application file for complete search history.

(56) References Cited

U.S. PATENT DOCUMENTS

| | | | |
|---|---|---|---|
| 4,997,929 A | 3/1991 | Collins et al. | 536/27 |
| 5,082,774 A | 1/1992 | Heinrich | 435/69.1 |
| 5,145,774 A | 9/1992 | Tarnowski et al. | 435/7.25 |
| 5,169,762 A | 12/1992 | Gray et al. | 435/69.1 |
| 5,196,315 A | 3/1993 | Ronnett et al. | 435/29 |
| 5,217,893 A | 6/1993 | Ronnett et al. | 435/240.21 |
| 5,272,063 A | 12/1993 | Chan et al. | 435/69.1 |
| 5,308,763 A | 5/1994 | Ronnett et al. | 435/240.21 |
| 5,338,839 A | 8/1994 | McKay et al. | 536/235 |
| 5,491,084 A | 2/1996 | Chalfie et al. | 435/189 |
| 5,502,176 A | 3/1996 | Tenen et al. | 536/24.1 |
| 5,753,506 A | 5/1998 | Johe | 435/377 |
| 5,874,304 A | 2/1999 | Zolotukhin et al. | 435/366 |
| 6,245,564 B1 | 6/2001 | Goldman et al. | 435/368 |
| 6,361,996 B1 * | 3/2002 | Rao et al. | 435/353 |

FOREIGN PATENT DOCUMENTS

| | | |
|---|---|---|
| WO | WO 94/09119 | 4/1994 |
| WO | WO 96/38541 | 12/1996 |
| WO | WO 96/38576 | 12/1996 |
| WO | WO 97/07200 | 2/1997 |
| WO | WO 98/32879 | 7/1998 |
| WO | WO 99/29279 | 6/1999 |

OTHER PUBLICATIONS

Wang et al., Isolation and Purification of Oligodendrocyte Progenitor Cells from the Adult Human Subcortex, Annals of Neurology, 44: 438, Sep. 1998.*

Arnstrong et al., Pre-Oligodendrocytes from Adult Human CNS, Journal of Neuroscience 12 (4): 1538-1547, Apr. 1992.*

(Continued)

*Primary Examiner* — Richard Hutson
(74) *Attorney, Agent, or Firm* — LeClairRyan, a Professional Corporation (57) ABSTRACT

The present invention is directed to a method of separating oligodendrocyte cells or progenitor cells thereof from a mixed population of cells. It comprises selecting a promoter which functions only in the oligodendrocyte cells or progenitor cells thereof, introducing a nucleic acid molecule encoding a fluorescent protein under control of that promoter into the mixed population cells, allowing the oligodendrocyte cells or progenitor cells thereof to express the fluorescent protein, and separating the fluorescent cells from the mixed population cells, where the separated cells are the oligodendrocyte cells or progenitor cells thereof. The invention also relates to the isolated and enriched human oligodendrocyte cells or progenitor cells thereof.

18 Claims, 7 Drawing Sheets

Identification and Enrichment of Oligodendrocyte Progenitor Cells from Adult Human Forebrain

OTHER PUBLICATIONS

Kirschenbaum et al. In vitro Neuronal Production and Differentiation by Precursor Cells Derived from the Adult Human Forebrain, Cerebral Cortex 6: 576-589, Nov. 1994.*

Scherer et al., "Differential Regulation of the 2',3'-Cyclic Nucleotide 3'-Phosphodiesterase Gene During Oligodendrocyte Development" *Neuron* 12:1363-1375 (1994).

Singh et al., "Identification, Isolation, and Promoter-Defined Separation of Mitotic Oligodendrocyte Progenitor Cells from the Adult Human Subcortical White Matter," *The Journal of Neuroscience* 19(22):9986-9995 (1999).

Schatz et al., "Two Functional alpha-tubulin Genes of the Yeast *Saccharomyces cerevisiae* Encode Divergent Proteins," *Mol. Cell Biol.*, 6(11):3711-21 (1986) (abstract).

Largent et al., "Directed Expression of an Oncogene to Olfactory Neuronal Lineage in Transgenic Mice," *J. Neurosci* 13(1):300-312 (1993).

Gloster et al., "The T alpha 1 alpha-tubulin Promoter Specifies Gene Expression as a Function of Neuronal Growth and Regeneration in Transgenic Mice," *J. Neurosci.*, 14(12):7319-30 (1994).

Angelichio et al., "Comparison of Several Promoters and Polyadenylation Signals for Use in Heterologous Gene Expression in Cultured *Drosophila* Cells," *Nuc. Acids Res.*, 19(18):5037-43 (1991).

Schatz et al., "Isolation and Characterization of Conditional-lethal Mutations in the TUB1 alpha-tubulin Gene of the Yeast *Saccharomyces cerevisiae*," *Genetics*, 120(3):681-95 (1988).

Schatz et al., "Insertions of up to 17 Amino Acids into a Region of alpha-tubulin Do Not Disrupt Function in Vivo," *Mol. Cell Biol.*, 7(10):3799-805 (1987).

Schatz et al., "Genetically Essential and Nonessential alpha-tubulin Genes Specify Functionally Interchangeable Proteins," *Mol. Cell Biol.*, 6(11):3722-33 (1986).

Nunes et al., "Identification and Isolation of Multipotential Neural Progenitor Cells from the Subcortical White Matter of the Adult Human Brain," *Nature Medicine* 9(4):439-447 (2003).

* cited by examiner

METHOD FOR ISOLATING AND PURIFYING OLIGODENDROCYTES AND OLIGODENDROCYTE PROGENITOR CELLS

This application claims the benefit of U.S. Provisional Patent Application Ser. No. 60/104,809 filed Oct. 19, 1998.

FIELD OF THE INVENTION

The present invention relates generally to a method of separating cells of interest, in particular oligodendrocyte cells, from brain tissue.

BACKGROUND OF THE INVENTION

Throughout this application various publications are referenced, many in parenthesis. Full citations for these publications are provided at the end of the Detailed Description. The disclosures of these publications in their entireties are hereby incorporated by reference in this application.

The damaged brain is largely incapable of functionally significant structural self-repair. This is due in part to the apparent failure of the mature brain to generate new neurons (Korr, 1980; Sturrock, 1982). However, the absence of neuronal production in the adult vertebrate forebrain appears to reflect not a lack of appropriate neuronal precursors, but rather their tonic inhibition and/or lack of post-mitotic trophic and migratory support. Converging lines of evidence now support the contention that neuronal and glial precursor cells are distributed widely throughout the ventricular subependymal of the adult vertebrate forebrain, persisting across a wide range of species groups (Goldman and Nottebohm, 1983; Reynolds and Weiss, 1992; Richards et al., 1992; Kirschenbaum et al., 1994; Kirschenbaum and Goldman, 1995a; reviewed in Goldman, 1995; Goldman, 1997; Goldman, 1998; Goldman and Luskin, 1998; and Gage et al., 1995). Most studies have found that the principal source of these precursors is the ventricular zone (Goldman and Nottebohm, 1983; Goldman, 1990; Goldman et al., 1992; Lois and Alvarez-Buylla, 1993; Morshead et al., 1994; Kirschenbaum et al., 1994; Kirschenbaum and Goldman, 1995), though competent neural precursors have been obtained from parenchymal sites as well (Richards et al., 1992; Palmer et al., 1995; Pincus et al., 1998). In general, adult progenitors respond to epidermal growth factor (EGF) and basic fibroblast growth factor (bFGF) with proliferative expansion (Reynolds and Weiss, 1992; Kilpatrick and Bartlett, 1995; Kuhn et al., 1997), may be multipotential (Vescovi et al., 1993; Goldman et al., 1996), and persist throughout life (Goldman et al., 1996). In rodents and humans, their neuronal daughter cells can be supported by brain-derived neurotrophic factor (BDNF) (Kirschenbaum and Goldman, 1995a), and become fully functional in vitro (Kirschenbaum et al., 1994, Pincus et al., 1998a, and Pincus et al. 1998b), like their avian counterparts (Goldman and Nedergaard, 1992).

A major impediment to both the analysis of the biology of adult neural precursors, and to their use in engraftment and transplantation studies, has been their relative scarcity in adult brain tissue, and their consequent low yield when harvested by enzymatic dissociation and purification techniques. As a result, attempts at either manipulating single adult-derived precursors or enriching them for therapeutic replacement have been difficult. The few reported successes at harvesting these cells from dissociates of adult brain, whether using avian (Goldman et al., 1992; 1996c), murine (Reynolds and Weiss, 1992), or human (Kirschenbaum et al., 1994) tissue, have all reported <1% cell survival. Thus, several groups have taken the approach of raising lines derived from single isolated precursors, continuously exposed to mitogens in serum-free suspension culture (Reynolds and Weiss, 1992; Morshead et al., 1994; Palmer et al., 1995). As a result, however, many of the basic studies of differentiation and growth control in the neural precursor population have been based upon small numbers of founder cells, passaged greatly over prolonged periods of time, under constant mitogenic stimulation. The phenotypic potential, transformation state and karyotype of these cells are all uncertain; after repetitive passage, it is unclear whether such precursor lines remain biologically representative of their parental precursors, or instead become transformants with perturbed growth and lineage control.

In order to devise a more efficient means of isolating native, unpassaged and untransformed progenitor cells from brain tissue, a strategy by which brain cells could be freely dissociated from brain tissue, then transduced in vitro with plasmid DNA bearing a fluorescent reporter gene under the control of neural progenitor cell-type specific promoters was developed (Wang et al., 1998). This permitted isolation of the elusive neuronal progenitor cell of the CNS, using the Tα1 tubulin promoter, a regulatory sequence expressed only in neuronal progenitor cells and young neurons.

The repair of damaged brain requires not only sources of new neurons but also new glial support cells. Oligodendrocytes are the glial cell type that produce myelin and insulate neuronal axons by ensheathment with myelin-bearing cell processes. Like neurons, oligodendrocytes are largely post-mitotic and cannot regenerate through proliferative expansion. However, persistent oligodendrocyte progenitors have been described in adult rodent subcortical white matter, and may provide a substrate for remyelination after demyelinating injury (Gensert, 1996; Gensert, 1997). In humans, the demonstration and identification of analogous subcortical oligodendrocyte progenitor cells has been problematic. A pre-oligodendrocytic phenotype has been described in adult human subcortical white matter, though these postmitotic cells may have included mature oligodendrocytes recapitulating their developmental program after dissociation (Armstrong, 1992). Rare examples of oligodendrocytes derived from mitotic division have also been reported in human subcortical dissociates (Scolding, 1995), but the identification and isolation of their mitotic progenitors have proven elusive. As a result, the enrichment of these cells for functional utilization has proven difficult. In particular, the cells have not been preparable in the numbers or purity required for in vivo engraftment into demyelinated recipient brain, whether experimentally or for clinical therapeutic purposes.

A strong need therefore exists for a new strategy for identifying, separating, isolating and purifying native oligodendrocyte precursor cells from brain tissue. Such isolated, enriched native precursors may be used in engraftment and transplantation in demyelinating disorders, as well as for studies of growth control and functional integration.

SUMMARY OF INVENTION

To this end, the subject invention provides a method of separating Oligodendrocytes or progenitor cells thereof from a mixed population of cells, based upon cell type-selective expression of cell-specific promoters. This method includes selecting a promoter which functions only in the oligodendrocyte cells or progenitor cells thereof, then introducing a nucleic acid molecule encoding a fluorescent protein under control of that promoter into the mixed population of cells, allowing the oligodendrocyte cells or progenitor cells thereof to express the fluorescent protein, and separating the fluorescent cells from the mixed population of cells, where the separated cells are the oligodendrocyte cells or progenitor cells thereof.

Another aspect of the invention relates to the isolated oligodendrocyte cells or progenitors thereof.

A promoter is chosen which specifically drives expression in oligodendrocyte cells or progenitor cells thereof but not in other cells of the nervous system. The fluorescent protein will therefore only be expressed and detectable in cells in which the promoter operates, i.e. those cells for which the promoter is specific.

The method involves the introduction of nucleic acid encoding the fluorescent protein, under the control of the cell specific promoter, into a plurality of cells. Various methods of introduction known to those of ordinary skill in the art can be utilized, including (but not limited to) viral mediated transformation (e.g., adenovirus mediated transformation), electroporation, and liposomal mediated transformation.

After cell specific expression of the fluorescent protein, such as green fluorescent protein (GFP), the cells expressing the fluorescent protein are separated by an appropriate means. In particular, the cells can be separated by fluorescence activated cell sorting. The method of the subject invention thus provides for the enrichment and separation of the oligodendrocyte cells or progenitor cells thereof.

Figure 1:
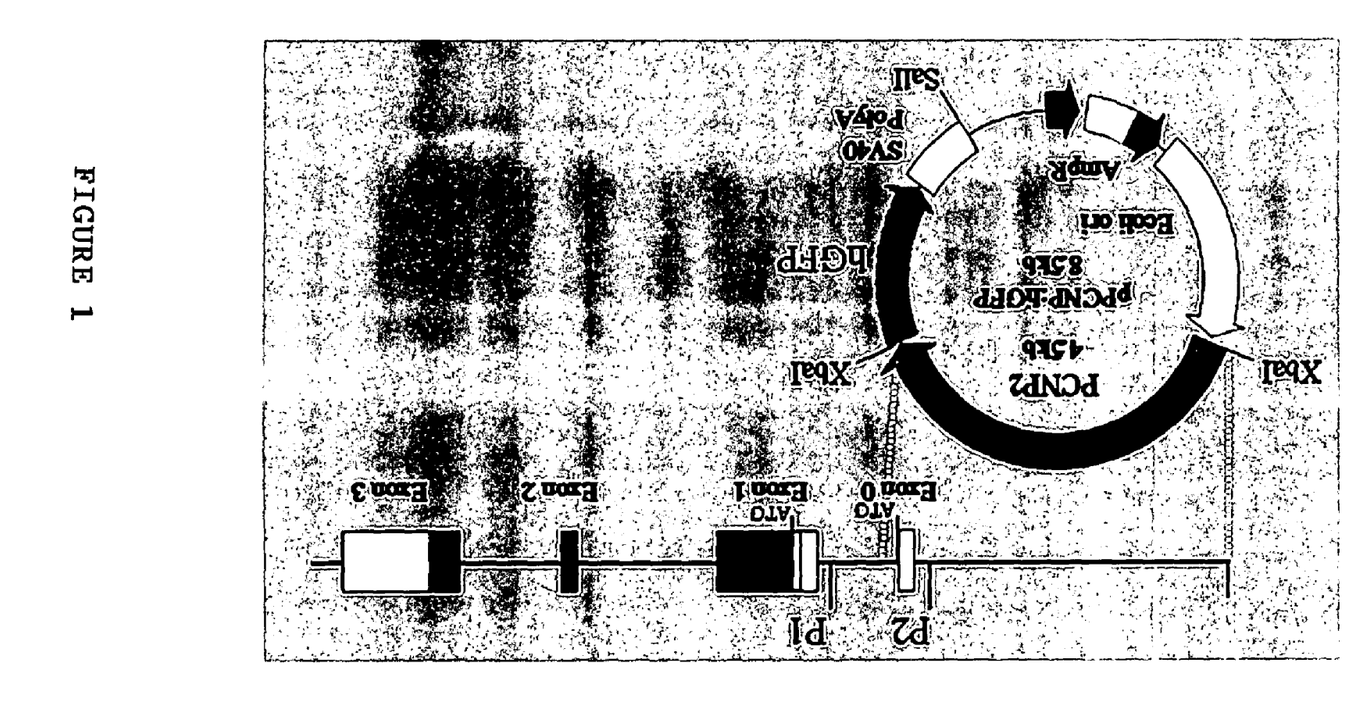

Contemporary approaches toward the use of neural precursor cells have focused upon preparing clonal lines derived from single progenitors. However, such propagated lines can become progressively less representative of their parental precursors with time and passage in vitro. To circumvent these difficulties, the method of the subject invention provides a strategy for the live cell identification, isolation and enrichment of native oligodendrocyte precursors and their oligodendrocyte daughter cells, by fluorescence-activated cell sorting of subcortical white matter cells transfected with fluorescent protein, driven by the oligodendrocyte-specific early promoter (P2) for cyclic nucleotide phosphodiesterase (CNP) (this promoter is hereinafter referred to as P/CNP2). Using this approach, oligodendrocyte precursors and their young oligodendrocyte daughters can be identified and selectively harvested from a wide variety of samples, including embryonic and adult brain of avian, mammalian, and human origin. This approach allows for the enrichment of neural precursors from both adults and embryos, with a yield substantially higher than that achievable through standard techniques of selective dissection and differential centrifugation. CNP protein, 2',3'-cyclic nucleotide 3'-phosphodiesterase (CNP; EC 3.1.4.37) (Tsukada, et al., 1992; Vogel et al., 1988, which are hereby incorporated by reference), is one of the earliest known myelin-associated proteins to be synthesized in developing oligodendrocytes. It is expressed by newly generated cells of oligodendrocytic lineage even within the ventricular zone, and appears to be expressed by their precursors as well, in both rodents and humans (Scherer et al., 1994; Yu et al., 1994; Peyron et al., 1997; Grever et al., 1997, which are hereby incorporated by reference). Importantly, the 5' regulatory region of the CNP gene includes 2 distinct promoters, P2 and P1, that are associated with 2 distinct RNAs, and are sequentially activated at different developmental stages (Douglas et al., 1992; Douglas and Thompson, 1993; Monoh et al., 1993; Scherer et al., 1994, which are hereby incorporated by reference) (FIG. 1). Only the CNP mRNA transcripted from the more upstream promoter, or P2 is found in the fetal brain, suggesting that the P2 promoter (P/CNP2) directs expression to young Oligodendrocytes and their precursors (Gravel et al., 1998; O'Neill et al., 1997, which are hereby incorporated by reference). As a result, the CNP2 promoter was chosen for this study for its ability to target transgene expression to oligodendrocyte progenitors and their immature progeny.

Extension of this approach to include fluorescent transgenes under the control of stage- and phenotype-specific promoters (both of which are intended to be covered by reference to "cell-specific" promoters herein) allows even more specific separations to be performed, for example, of oligodendrocytes over a range of developmental stages. More broadly, this strategy may be applied to any tissue of interest for which a cell-specific promoter is available, thereby allowing the identification, isolation and separation of progenitor cells and their products from any tissue for which constituent cells have been assigned phenotype-selective promoters. This strategy permits sufficient enrichment for in vivo implantation of the defined and separated progenitor pools, as well as for in vitro analyses of phenotypic specification and growth control.

By providing a means of identifying oligodendrocytic precursors while alive, even when present in small numbers in mixed populations, the use of fluorescent transgenes driven by cell type-selective promoters such as P/CNP2 will allow the specification of phenotype to be studied and perturbed on the single cell level, an approach that had previously only been feasible on larger populations. Indeed, when used in conjunction with post-transfection FACS, this strategy may permit the enrichment of any cell type for which stage- or phenotype-specific promoters are available. For instance, similar GFP constructs based upon early neuronal promoters, such as T$\alpha$1 tubulin (Wang et al., 1998), might similarly permit the enrichment of neuronal as well as oligodendrocytic precursors from adult brain tissue. As a result, spectrally distinct GFP variants with non-overlapping emission spectra (Heim and Tsien, 1996), each driven by a different cell-specific promoter, will allow concurrent identification of neuronal and oligodendrocytic precursors in vitro. Multi-channel cell sorting based upon the concurrent use of several lasers with non-overlapping excitation lines, such as Ar—K and He—Ne, should then allow the separation and simultaneous isolation of several distinct precursor phenotypes from a given brain sample.

By providing a means to identify and enrich viable oligodendrocytic precursor cells, from adult as well as fetal brain, this strategy may allow a significant acceleration in the study of precursor and stem cell biology. In particular, it may allow the preparation and enrichment of both oligodendrocytic and other neural precursor cells in sufficient number to permit implantation and engraftment using native, unpassaged adult-derived progenitor cells. This approach may spur the development of induced adult oligoneogenesis as a viable therapeutic modality for the structural repair of the damaged or demyelinated central nervous system, whether in the brain or spinal cord. In particular, the potential use of these cells as substrates for induced remyelination, whether upon endogenous activation or engraftment, suggests therapeutic strategies appropriate to a variety of white matter diseases. These potential therapeutic targets include ischemic demyelination, as in subcortical lacunar infarction and hypertensive leukoencephalopathy, post-inflammatory demyelinations, such as radiation necrosis and remitted multiple sclerosis, as well as the degenerative and metabolic leukodystrophies.

BRIEF DESCRIPTION OF THE DRAWINGS

These and other features and advantages of this invention will be evident from the following detailed description of preferred embodiments when read in conjunction with the accompanying drawings in which:

FIG. 1 shows the human P/CNP2:hGFP vector. Humanized GFP (Levy, et al., 1996), a mutant form of red-shifted GFP optimized for expression in human cells, was placed under the control of the human CNP2 promoter (P/hCNP2; Gravel, et al., 1996). To construct P/hCNP2:hGFP, an XbaI-XbaI fragment encompassing exon 0 and part of intron 1 was isolated from the SK/hgCNP plasmid, which contains the complete sequence of the human CNP gene (Gravel, et al., 1996), and was then linked to the hGFP gene fused to the SV40 polyadenylation signal.

FIGS. 2A-C show a typical bipolar cell, double labeled for A2B5 (red) and BrdU (yellow), fixed after 4 DIV. FIGS. 2D-F show a cluster of postmitotic O4$^+$ cells (FIGS. 2D-E) and an overtly less mature BrdU-incorporating O4$^+$/BrdU$^+$ cell (FIG. 2F), all fixed after 7 DIV. FIGS. 2G-I show representative examples of the diverse phenotypes present in the adult white matter. These included cells expressing CNP (FIG. 2G), GFAP (FIG. 2H), and TuJ1 (FIG. 2I)—immunoreactivities, which respectively identify Oligodendrocytes, astrocytes, and neurons; each cell type was found in the proportion noted in the text.

FIGS. 3A-F show P/hCNP2:hGFP-expressing cells (FIGS. 3A, C, E) and their corresponding phase contrast micrographs (FIGS. 3B, D, F). FIGS. 3G-H show immunocytochemistry identified the P/hCNP2:hGFP$^+$ bipolar cells as A2B5$^+$. The inset in FIG. 3H shows that this cell incorporated BrdU.

FIG. 4 shows that culturing, isolation, and enrichment of oligodendrocyte progenitors. Adult human subcortical white matter, derived from surgical samples of frontal and temporal lobe, was dissected and enzymatically dissociated using papain and DNase, then cultured and transfected with either P/hCNP2:hGFP or control plasmids (hP/CMV:hGFP and P/hCNP2:lacZ).

FIGS. 5A-B show a representative sort of a human white matter sample, derived from the frontal lobe of a 42 year-old woman during repair of an intracranial aneurysm. This plot shows 50,000 cells (sorting events) with their GFP fluorescence intensity plotted against their forward scatter (a measure of cell size). FIG. 5A indicates the result obtained from a nonfluorescent P/hCNP2:lacZ-transfected control, while FIG. 5B indicates the corresponding result from a matched culture transfected with P/hCNP2:hGFP. FIGS. 5C and D show phase and fluorescence images of GFP$^+$ cells before (FIG. 5C) and 2 hrs after (FIG. 5D) sorting.

FIGS. 6A-C show a bipolar A2B5$^+$/BrdU$^+$ cell, 48 hrs after FACS. FIGS. 6D-F show that within 3 weeks the bipolar cells matured into fibrous, O4$^+$ cells. These cells often incorporated BrdU, indicating their in vitro origin from replicating A2B5$^+$ cells. FIGS. 6G-I show a multipolar oligodendrocyte expressing CNP, still expressing GFP 3 weeks after FACS.

FIGS. 7A-B show P/hCNP2:hGFP-sorted cells express O4 (red) and begin process elaboration within 4 days after FACS. FIGS. 7C-D show that by 2 weeks post-FACS, these cells generally develop multipolar morphologies. red., O4-immunoreactive cells. FIGS. 7E-F show that progenitor derived-cells matured further over the following weeks, developing oligodendrocytic morphologies and both CNP protein and galactocerebroside expression by 4 weeks in vitro.

DETAILED DESCRIPTION

A plasmid designated pGFP 10.1 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 75547 on Sep. 1, 1993. This plasmid is commercially available from the ATCC due to the issuance of U.S. Pat. No. 5,491,084 on Feb. 13, 1996 in which the plasmid is described. This plasmid comprises a cDNA which encodes a green fluorescent protein (GFP) of *Aequorea victoria* as disclosed in U.S. Pat. No. 5,491,084 to Chalfie et al., the contents of which are incorporated herein by reference.

The plasmid designated pTα1-RSGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 98298 on Jan. 21, 1997. This plasmid uses the red shifted GFP (RS-GFP) of Clontech Laboratories, Inc. (Palo Alto, Calif.), and the Tα1 promoter sequence provided by Dr. F. Miller (Montreal Neurological Institute, McGill University, Montreal, Canada). In accordance with the subject invention, the Tα1 promoter can be replaced with another specific promoter, and the RS-GFP gene can be replaced with another form of GFP, by using standard restriction enzymes and ligation procedures.

The plasmid designated pTα1-hGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 98299 on Jan. 21, 1997. This plasmid uses the humanized GFP (GFPh) of Zolotukhin and Muzyczka (Levy et al. 1996b), and the Tα1 promoter sequence provided by Dr. F. Miller (Montreal). In accordance with the subject invention, the Tα1 promoter can be replaced with another specific promoter, and the GFPh gene can be replaced with another form of GFP, by using standard restriction enzymes and ligation procedures.

The plasmid designated pCNP2-hGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 98934 on Oct. 20, 1998.

The plasmid designated pCNP(1+2)-hGFP has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 98935 on Oct. 20, 1998.

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

The subject invention provides a method of separating oligodendrocyte cells or progenitor cells thereof from a mixed population of cells, based upon cell type-selective expression of cell specific promoters. This method includes selecting a promoter which functions only in the oligodendrocyte cells or progenitor cells thereof, introducing a nucleic acid molecule encoding a fluorescent protein under control of the promoter into the mixed population of cells, allowing the oligodendrocyte cells or progenitor cells thereof to express the fluorescent protein; and separating the fluorescent cells from the mixed population of cells, where the separated cells are the oligodendrocyte cells or progenitor cells thereof.

The cells of particular interest according to the subject invention are oligodendrocyte cells, more particularly oligodendrocyte precursor cells. Any cell which one desires to separate from a plurality of cells can be chosen according to the subject invention, as long as a promoter specific for the chosen cell is available. "Specific", as used herein to describe a promoter, means that the promoter functions only in the chosen cell type. A chosen cell type can refer to different types of cells, or different stages in the developmental cycle of a cell.

Illustrative of possible cell and promoter combinations which can be used in the subject invention are the following: a mature oligodendrocyte and a cyclic nucleotide phosphodiesterase I (i.e. CNPase I) promoter (Scherer et al. 1994); a myelinating oligodendrocyte and a myelin basic protein promoter (Wrabetz et al. 1993); an oligodendrocyte and a JC virus minimal core promoter (Krebs et al. 1995); a myelinating oligodendrocyte and a proteolipid protein promoter (Cambi and Kamholz 1994); or an oligodendrocyte progenitor and a cyclic nucleotide phosphodiesterase II (i.e. P/CNP2) promoter (Scherer et al. 1994). Preferably, the cell of interest is an oligodendrocyte or progenitor cell thereof and the promoter is P/CNP2.

Having determined the cell of interest and selected a promoter specific for the cell of interest, a nucleic acid molecule encoding a fluorescent protein, preferably a green fluorescent protein, under the control of the promoter is introduced into a plurality of cells to be sorted.

The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (U.S. Pat. No. 5,491,084). A plasmid encoding the GFP of *Aequorea victoria* is available from the ATCC as Accession No. 75547. A mutated form of this GFP (a red-shifted mutant form) designated pRSGFP-C1 is commercially available from Clontech Laboratories, Inc. (Palo Alto, Calif.).

Mutated forms of GFP that emit more strongly than the native protein, as well as forms of GFP amenable to stable translation in higher vertebrates, are now available and can be used for the same purpose. The plasmid designated pTα1-GFPh (ATCC Accession No. 98299) includes a humanized form of GFP. Indeed, any nucleic acid molecule encoding a fluorescent form of GFP can be used in accordance with the subject invention. Furthermore, any nucleic acid molecule encoding an enzyme that can catalyze the conversion of a fluorgenic substrate to a fluorophone can be used in accordance with the subject invention. An example is the use of a cell-specific promoter to drive lacZ expression, with the detection and sorting of lacZ-expressing cells being by means of incubation with the fluorogenic substrates FDG (fluorescein-β-D-galactopyranoside) or CMFDG (chloromethyl-FDG).

Standard techniques are then used to place the nucleic acid molecule encoding GFP under the control of the chosen cell specific promoter. Generally, this involves the use of restriction enzymes and ligation (see below).

The resulting construct, which comprises the nucleic acid molecule encoding the GFP under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses and lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

In accordance with one of the above-described methods, the nucleic acid molecule encoding the GFP is thus introduced into a plurality of cells. The promoter which controls expression of the GFP, however, only functions in the cell type of interest. Therefore, the GFP is only expressed in the cell type of interest. Since GFP is a fluorescent protein, the cells of interest can therefore be identified from among the plurality of cells by the fluorescence of the GFP.

Any suitable means of detecting the fluorescent cells can be used. The cells may be identified using epifluorescence optics, and can be physically picked up and brought together by Laser Tweezers (Cell Robotics Inc., Albuquerque, N. Mex.). They can be separated in bulk through fluorescence activated cell sorting, a method that effectively separates the fluorescent cells from the non-fluorescent cells (e.g., Wang et al., 1998).

The method of the subject invention thus provides for the isolation and enrichment of oligodendrocyte precursors from embryonic and adult brain of both fetal and adult, rodent and human derivation. Specifically, fluorescence-activated cell sorting of subependymal and subcortical white matter cells transfected with green fluorescent protein driven by the oligodendrocyte P/CNP2 promoter is provided. CNPase is localized almost exclusively to the nervous system, in which it appears specific for oligodendrocytes (Scherer et al., 1994). Though most abundant in young neurons extending neurites, it is first expressed earlier in neuronal ontogeny, including in VZ cells (Gravel et al., 1988). The 4.5 kb 5' flanking region from the CNPase gene contains those sequence elements responsible for specifying CNPase expression to developing oligodendrocytes, and for regulating its expression as a function of growth (Scherer et al., 1994; Gravel et al., 1998). Transgenic mice with the 4.5 kb 5' flanking region fused to a nuclear lacZ reporter manifested expression of the CNPase promoter-driven transgene only within developing oligodendrocytes within the central nervous system, suggesting that CNPase promoter was expressed by oligodendrocytic precursor cells, as well as their young neuronal progeny.

The oligodendrocytic specificity and early expression of the CNPase promoter was capitalized on to use it as a marker for new oligodendrocytes and their parental precursors. This was done by coupling the CNPase promoter to the red-shifted mutant form of green fluorescent protein (Chalfie et al., 1994; Heim and Tsien, 1996), and transfecting both embryonic and adult forebrain subcortical cells with the resulting construct. These cells were successfully transfected with several liposomal techniques, including Lipofectin (Life Technologies, Grand Island, N.Y.), and Effectin (Qiagen), as well as with an adenoviral vector bearing GFP. These techniques are particularly appropriate for transfecting CNP:GFP into large, mixed cell populations.

Two days after transfection, CNP2 expressing white matter cells, largely either young oligodendrocytes or their oligodendrocyte-specified progenitors, were then identified on the basis of their GFP fluorescence to blue excitation. This approach allowed for the identification and observation, alive and in real time, of VZ precursor cells and their neuronal daughters, derived from both fetal and adult brain. The brilliant fluorescence of these oligodendrocyte-driven GFP precursor cells permitted their isolation and selective enrichment by fluorescence activated cell sorting (FACS), which yielded cell populations highly enriched in young oligodendrocytes and their precursors; of the latter, many proceeded to differentiate as neurons in the days following their preparation.

The cells separated by the method of the present invention may be used in both basic analyses of oligodendrocyte precursor growth control, as well as in directly applied studies of their transplantability and engraftment characteristics. This approach permits oligodendrocyte progenitor engraftment for the remyelination of demyelinated foci, in both ischemic and inflammatory demyelinating diseases, such as subcortical infarction, hypertensive leukoencephalopathy, and multiple sclerosis, respectively. The cells similarly can be used in support of the structural repair of the damaged central nervous system, such as in the traumatized brain, or the contoured, traumatized, or transected or spinal cord.

EXAMPLES

Example 1

Materials and Methods

Plasmid Construction

P/hCNP2:hGFP and P/hCNP2:lacZ Humanized GFP (hGFP), a mutant form of GFP optimized for expression in human cells (Levy, et al., 1996, which is hereby incorporated by reference), was placed under the control of the human CNP2 promoter (Douglas, et al., 1992; Monoh, et al, 1993; and Gravel et al., 1996). The human CNP gene had been isolated previously (Gravel, et al., 1996), by screening a human fibroblast genomic library with a cDNA probe for rat CNP1. The human CNP gene was then subcloned into pBluescript, and the resultant plasmid was designated SK/hgCNP. This plasmid was digested with BgIII and XhoI to delete much of the gene downstream of the promoter region. The remaining BgIII and XhoI ends were then filled-in and blunt-end ligated, yielding plasmid SK/P1P2hCNP, in which both BgIII and XhoI were regenerated. A 1123 bp XhoI-XhoI fragment containing SV40 SD/SA-GFPh-SV40 poly(A) was then excised from pTα1:hGFP (Wang, et al., 1998), and subcloned into XhoI-digested SK/P1P2hCNP to generate the plasmid P1P2hCNP:hGFP. The orientation of the hGFP insert was then determined by restriction enzyme mapping.

To construct pP/hCNP2:hGFP, the Tα1 tubulin promoter region was excised from pP/Tα1:hGFP using XbaI, and replaced with the hCNP2 promoter obtained by digesting SK/hgCNP with XbaI. The orientation of hCNP2 insert was also determined by restriction enzyme mapping. Similarly, P2hCNP:lacZ was constructed by removing the Tα1 promoter from the Tα1:lacZ (Wang, et al., 1998) with XbaI, and replacing it with the XbaI-XbaI fragment containing the hCNP2 promoter. P/CMV:hGFP was constructed as previously reported Wang, et al., 1998).

Adult Human Brain White Matter Dissociation and Culture.

Adult human brain tissues obtained in the course of lobectomy of epilepsy patients was used here. The tissues were collected in $Ca^{2+}/Mg^{2+}$-free HBSS. The white matter was dissected from the rest of the tissue, cut into pieces of roughly 2 mm on edge, or 8 $mm^3$, and rinsed twice with PIPES solution (120 mM NaCl, 5 mM KCl, 25 mM glucose, 20 mM PIPES). It was then digested in pre-warmed papain/PIPES solution (11.4 U/ml papain, Worthington) and DNase I (10 U/ml, Sigma), on a rocking shaker for 1 hr at 37° C. The tissue was then collected by centrifuging at 200 g in an IEC Centra-4B centrifuge, resuspended in DMEM/F12/N2 with DNase I (10 U/ml), and incubated for 15 min at 37° C. The samples were again spun and their pellets recovered in 2 ml of DMEM/F12/N2. They were then dissociated by sequentially triturating for 20, 10, and 5 times, respectively, through 3 glass Pasteur pipettes fire polished to decreasing bore diameters. Undissociated tissue pieces were eliminated by passage through a fine 40 µm mesh. The cells were collected and rinsed once with DMEM/F12/N2 containing 20% platelet-depleted FBS (PD-FBS, Cocalico), to stop the enzymatic dissociation, and then resuspended at $1\times10^7$ cells/ml in DMEM/F12/N2 containing 10% FBS. The cell suspension was plated at 0.1 ml/dish into 35 mm Falcon Primaria plates coated with laminin (2 μg/cm$^2$) and incubated at 37° C. in 5% $CO_2$. After 4 hrs., an additional 0.7 ml of DMEM/F12/N2 with 2% PD-FBS was added into each plate. This medium was supplemented with IGF-1 (20 ng/ml; Sigma), FGF-2 (20 ng/ml; Sigma), NT-3 (20 ng/ml; Regeneron), and BrdU (10 nM). Following three days of incubation the cultures were switched to serum-free DMEM/F12/N2, with maintained growth factor and BrdU supplementation. Cultures were transfected at 7 DIV.

Transfection

All plasmid constructs were introduced into the cultured cells by liposomal transfection, as described Wang, et al., 1998. Briefly, 6 to 7 days after plating, each 35 mm dish received mixture of 2 μg of plasmid DNA and 10 μl of lipofectin in OPTI-MEM (GIBCO). The cells were incubated at 37° C. in 5% CO2/95% air for 6 hrs. The transfections were terminated with in DMEM/F12/N2 with 10% PD-FBS. After 2 hrs, the cells were returned into serum free DMEM/F12/N2 with PDGF AA and bFGF. Imaging for hGFP was first done 2 days after transfection, and daily thereafter, using an Olympus IX70 epifluorescence microscope. The greatest number and proportion of GFP$^+$ cells were observed 6-7 days after transfection; cultures were therefore sorted at that timepoint.

Flow Cytometry and Sorting

Flow cytometry and sorting of hGFP$^+$ cells was performed on a FACS Vantage (Becton-Dickinson). Cells ($5\times10^6$/ml) were analyzed by light forward and right-angle (side) scatter, and for GFP fluorescence through a 530±15 nm bandpass filter, as they traversed the beam of an argon ion laser (488 nm, 100 mW). P/hCNP2:lacZ-transfected control cells were used to set the background fluorescence; a false positive rate of 0.02±0.05% was accepted so as to ensure an adequate yield. For the test samples transfected with P/hCNP2:hGFP, cells having fluorescence higher than background were sorted at 3000 cells/sec. Sorted cells were plated onto laminin-coated 24-well plates, into DMEM/F12/N2 containing PDGF AA and FGF2, each at 20 ng/ml, and BrdU. After 4 days, some plates were fixed for immunocytochemistry, and the remainder switched to DMEM/F12/N2 containing 10% PD-FBS. After an additional 3 weeks in vitro, the sorted cells were stained for either CNP, O4, TuJ1, or GFAP-immunoreactivities; each was double-stained for BrdU as well.

Data Analysis

Experimental endpoints included the proportion of A2B5, O4, CNP, GFA, and TuJ1-immunoreactive cells in the total sorted population (all nominally GFP$^+$ following sorting), as a function of time after FACS. At each sampled time-point, the respective proportions of A2B5$^+$, O4$^+$, CNP$^+$, GFA$^+$, and TuJ1$^+$ cells were compared to each other, and to unsorted controls that were similarly dispersed but replated without sorting (after adjusting their cell densities to those of the post-FACS sorted pool). For each combination of treatment (sorted or unsorted), time-point (4 days and 3-4 weeks after FACS), and immunolabel (A2B5, O4, CNP, TuJ1, and GFA), the number of stained and unstained cells were counted in 10 randomly chosen fields, in each of 3 triplicate cultures.

Immunocytochemistry

Cells were immunostained live for A2B5 or O4, or following fixation with 4% paraformaldehyde, for CNP, TuJ1, GFAP, or BrdU. For A2B5 or O4 immunocytochemistry, plates were washed twice with DMEM/F12/N2, then blocked with DMEM/F12/N2 containing 5% normal goat sera (NGS) for 10 min at 4° C. Monoclonal antibody (MAb) A2B5 (clone 105, ATCC) was used as an undiluted culture supernatant, and mouse MAb O4 (Boehringer Mannheim) was used at 1:200. Both were applied in DMEM/F12/N2 for 30 min at 4° C. The plates were then washed with three changes of cold HBSS containing 1% NGS. The secondary antibody, Texas Red-conjugated goat anti-mouse IgM was used at a dilution of 1:50 for 30 min at 4° C. The cells were then washed and fixed with cold 4% paraformaldehyde for 10 min, washed, mounted in SlowFade and observed using an Olympus IX70 equipped for epifluorescence. Immunocytochemistry for GFAP and TuJ1 was performed according to described methods (Wang, et al., 1998), as was that for TuJ1 and BrdU (Luskin, et al., 1997).

Example 2

Dissociates of Adult Human White Matter Harbored a Pool of Bipolar, A2B5$^+$ Cells To fully characterize the cell phenotypes resident in adult human white matter, papain dissociates of surgically-resected frontal and temporal capsular white matter were obtained from 8 patients. These included 4 males and 4 females, who ranged from 24-65 years old. Three patients had temporal lobe resections for medication-refractory epilepsy; 2 were subjected to parenchymal excision during meningioma resection, 2 samples were taken during aneurysmal repair, and 1 was taken from the non-neoplastic approach to a histologically benign ganglioglioma. The monolayer cultures resulting from these white matter dissociations were stained after 5-7 days in vitro (DIV) for either of 2 oligodendrocytic markers, that included the epitopes recognized by the A2B5 and O4 antibodies. Additional, matched cultures were stained after 14 DIV, for either A2B5 or O4, for oligodendrocytic CNP protein, or for either neuronal (βIII-tubulin) or astrocytic (glial fibrillary acidic protein, GFAP) target antigens.

Figure 2:
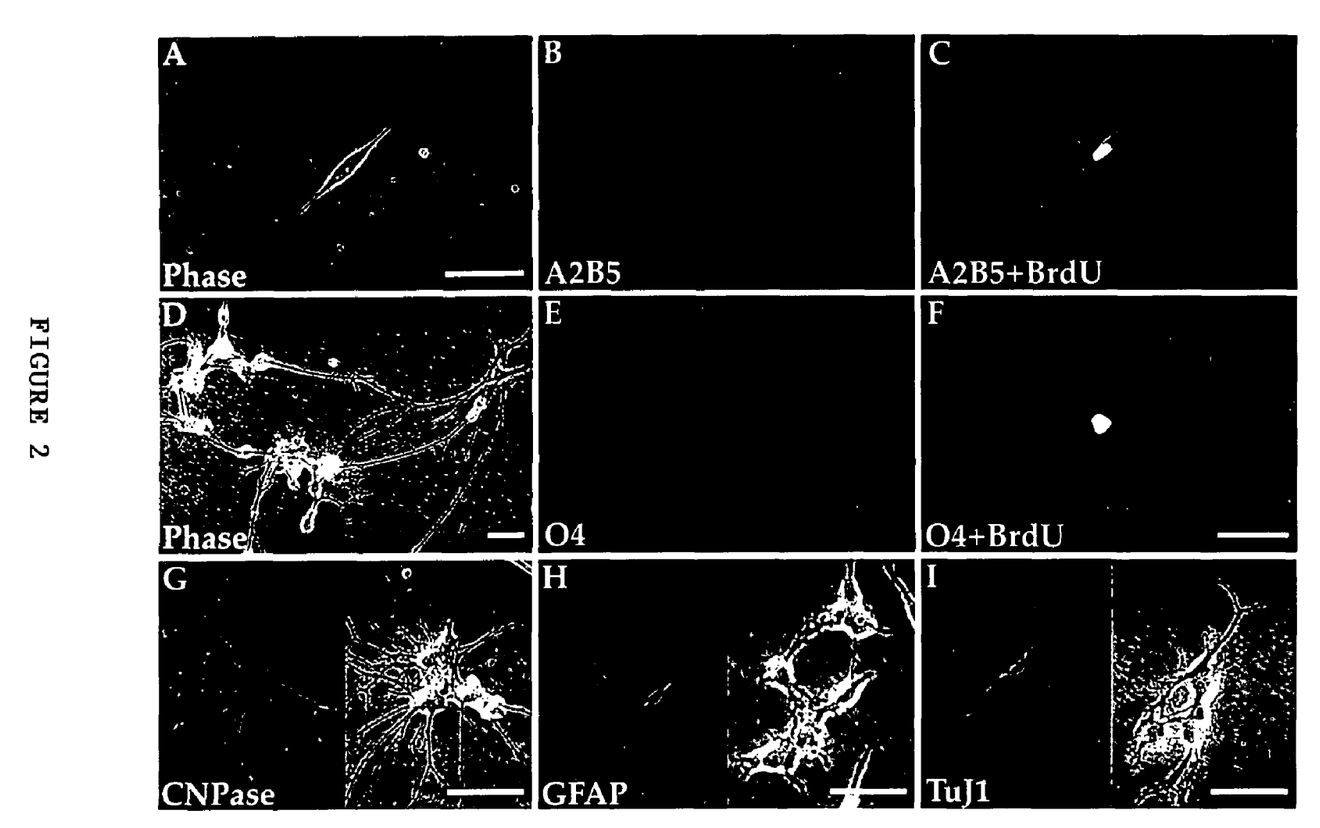
FIGS. 2A-I show that adult human white matter harbors oligodendrocyte progenitors. Immunocytochemistry of white matter dissociates for a panel of cell type-selective antigens revealed a diverse representation of phenotypes before sorting.

In the 14 DIV dissociates of subcortical white matter, 48.2±10.7% of the plated cells expressed the oligodendrocytic epitope recognized by MAb O4 (n=3 patients, with a combined total of 935 O4$^+$ cells among 2041 scored white matter cells) (FIG. 2). Similarly, 49.9±4.9% were immunoreactive for oligodendrocytic CNP protein. Another 7.3±3.2% expressed glial fibrillary acidic protein (GFAP). Double-labeling of selected plates revealed that the O4$^+$ and CNP$^+$ pools were largely overlapping, with a small proportion of CNP$^+$/O4$^-$ cells. In contrast, the GFA$^+$ cells only rarely included O4$^+$ examples. A small proportion of TuJ1$^+$ neurons (5.2±2.2%) was also observed. Through 30 DIV, the proportions of oligodendrocytes and neurons in these cultures remained roughly stable, with 51.3±7.0% O4$^+$ cells and 6.0±2.1% TuJ1$^+$ cells, respectively. In contrast, the proportion of GFA-defined astrocytes in these cultures increased from 7.3±3.2% at 14 DIV to 15.9±1.4% at 30 DIV (p<0.01 by Student's t-test). At each time point, the uncharacterized remainder of the total cell population included endothelial cells and microglia, whose numbers we did not quantify further.

Notably, a distinct population of small bipolar cells, that expressed A2B5, but which otherwise expressed neither neuronal nor oligodendrocytic phenotypic markers, was observed; these constituted 1.8±0.4% (n=5 patients) of all cultured white matter cells at 7 days. However, these cells became scarcer with time in vitro; by 30 DIV, A2B5$^+$ cells constituted <0.1% of the total cultured cell pool.

Example 3

The CNP2 Promoter Targeted GFP Expression to a Bipolar, A2B5$^+$ Phenotype

Figure 3:
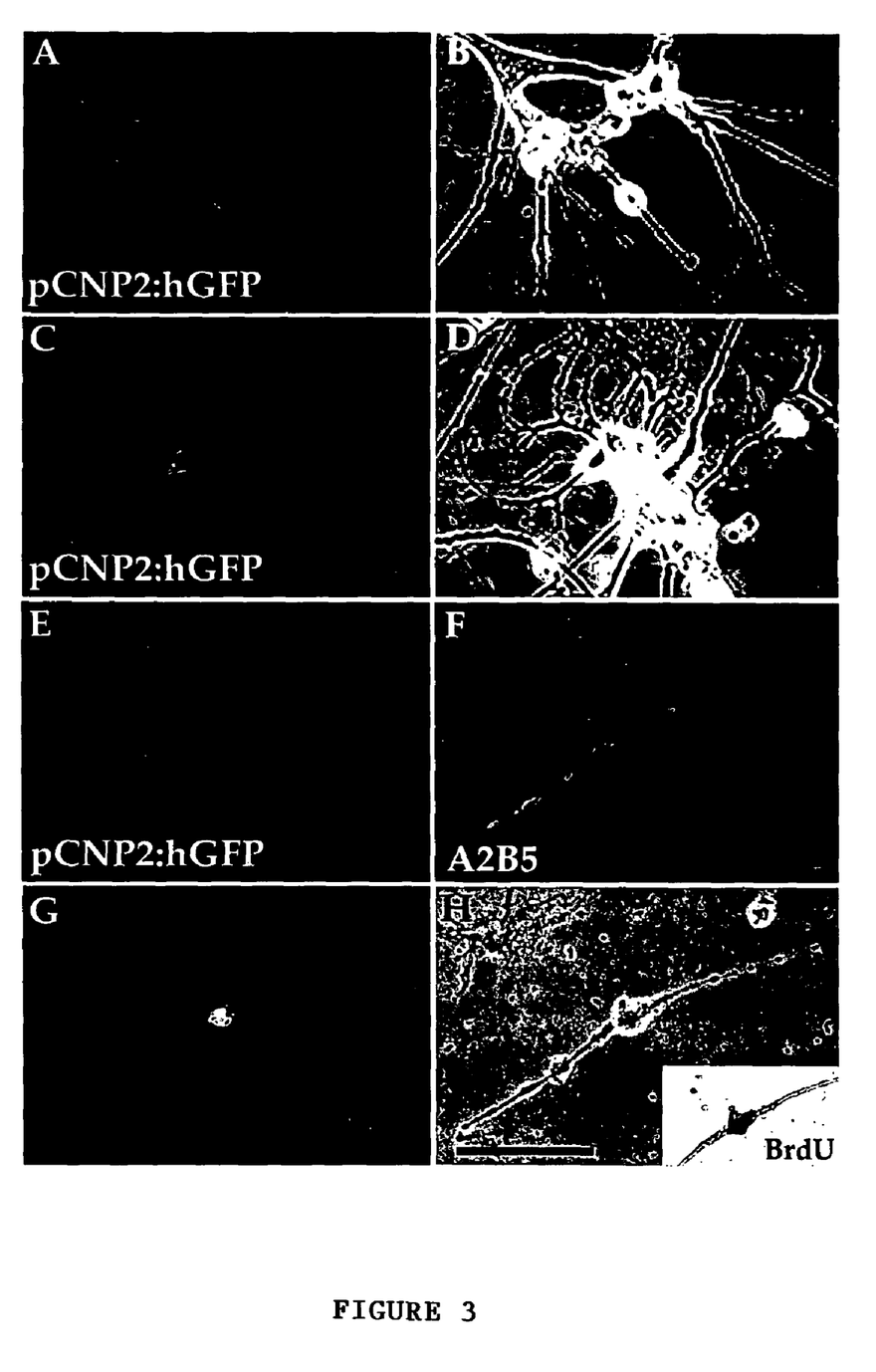
FIG. 3 shows that P/hCNP2:hGFP identifies a population of bipolar, A2B5$^+$ cells. GFP expression was observed within 4 to 5 days after transfection. The P/hCNP2:hGFP$^+$ cells typically first appeared as small, bipolar cells.

To identify either oligodendrocyte progenitor cells or their immature progeny, white matter dissociates were next transfected with plasmids encoding P/hCNP2:hGFP. Within 4 days after transfection with P/hCNP2:hGFP, a small proportion of GFP$^+$ cells were noted. These were invariably small, bipolar cells, and constituted <1% of the total cell pool (FIG. 3). After an additional 4-7 days in vitro, the cultures were immunostained for one of 3 oligodendrocyte lineage markers, which included A2B5, O4, and CNP protein, or for either astrocytic GFAP or neuronal βIII-tubulin. At that point, the cells could generally be described as A2B5$^+$/O4$^\pm$/GFAP$^-$/TuJ1$^-$: 62.5±8.8% of P/hCNP2:hGFP$^+$ cells expressed A2B5-IR, 21.1±7.5% were O4$^+$, and another 7.3±3.2% expressed astrocytic GFAP. None were recognized by MAb TuJ1, which targets neuronal βIII-tubulin (Menezes, et al., 1994, which is hereby incorporated by reference). Thus, within the first 7-10 days in culture, P/hCNP2:hGFP selectively identified a population of bipolar, A2B5$^+$ cells. When followed over the weeks thereafter, most of these P/hCNP2:hGFP$^+$ cells developed into oligodendrocytes, that could be recognized by their small, multipolar, heavily branching profiles. Indeed, by 4 weeks, most P/hCNP2:hGFP$^+$ cells expressed O4, while only rare cells (<1%) continued to express A2B5-IR.

Example 4

P/hCNP2:hGFP-Identified Cells were Mitotic In Vitro

Among white matter dissociates continuously exposed to BrdU and transfected with pP/hCNP2:hGFP on day 4 in vitro, 55±14.8% of the resultant P/hCNP2:hGFP$^+$ cells incorporated BrdU by day 7 (n=30 plates, derived from 3 patients) (FIG. 3). Similarly, 43.1±9.1% (n=5 plates) of the A2B5$^+$ cells in matched plates incorporated BrdU over the same time period. Morphologically, essentially all of these A2B5$^+$ and BrdU$^+$ cells were bipolar at 1 week (FIG. 2). In contrast, the large majority of morphologically mature oligo-dendrocytes failed to incorporate BrdU in vitro: Only 2.1±1.1% of O4$^+$ cells labeled with BrdU to which they were exposed during the first week in culture, and these few O4$^+$ cells may have just arisen from A2B5$^+$ forebears.

Example 5

FACS Segregated P/hCNP2:hGFP$^+$ Cells as Bipolar, A2B5$^+$ Progenitors

Figure 4:
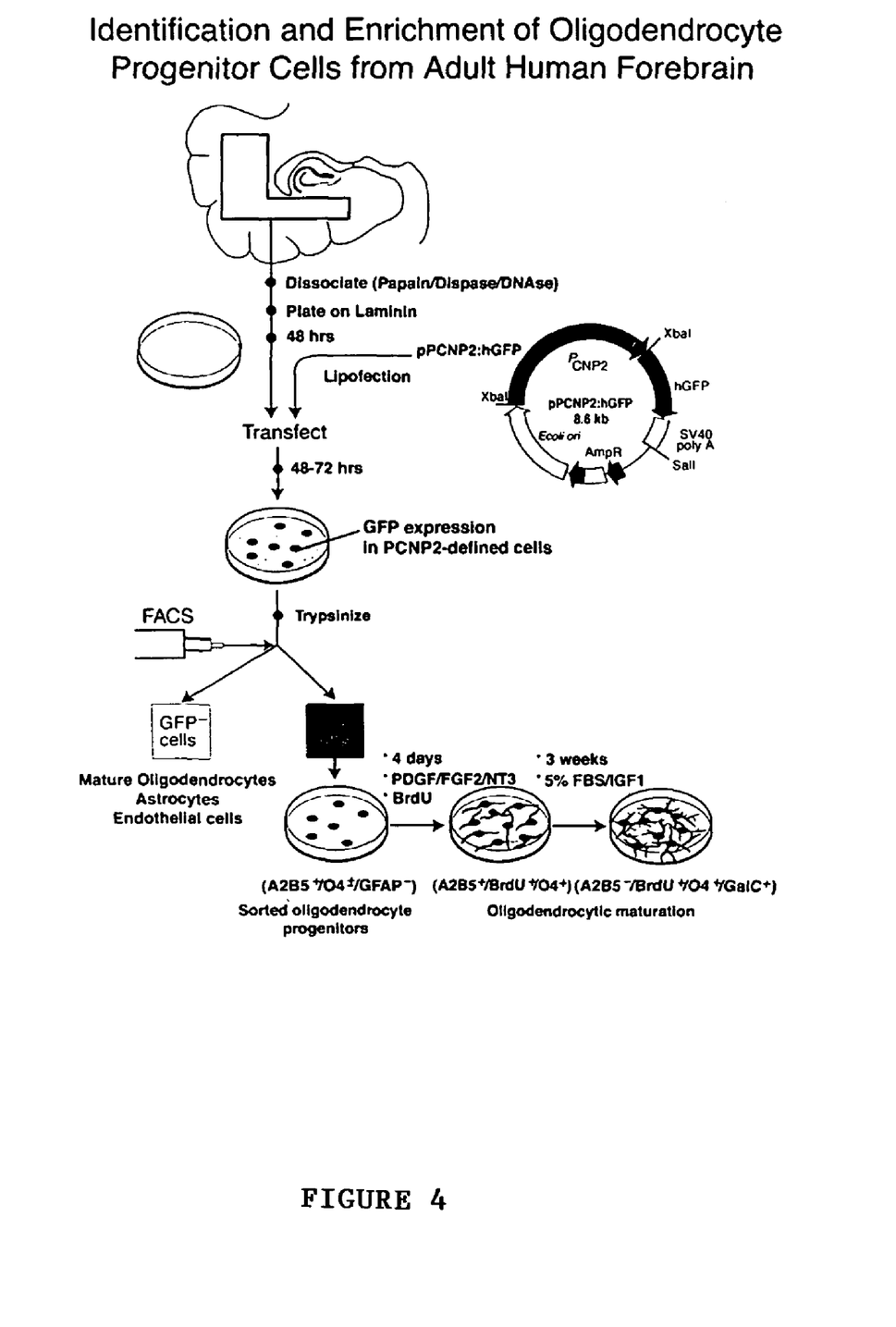
Figure 5:
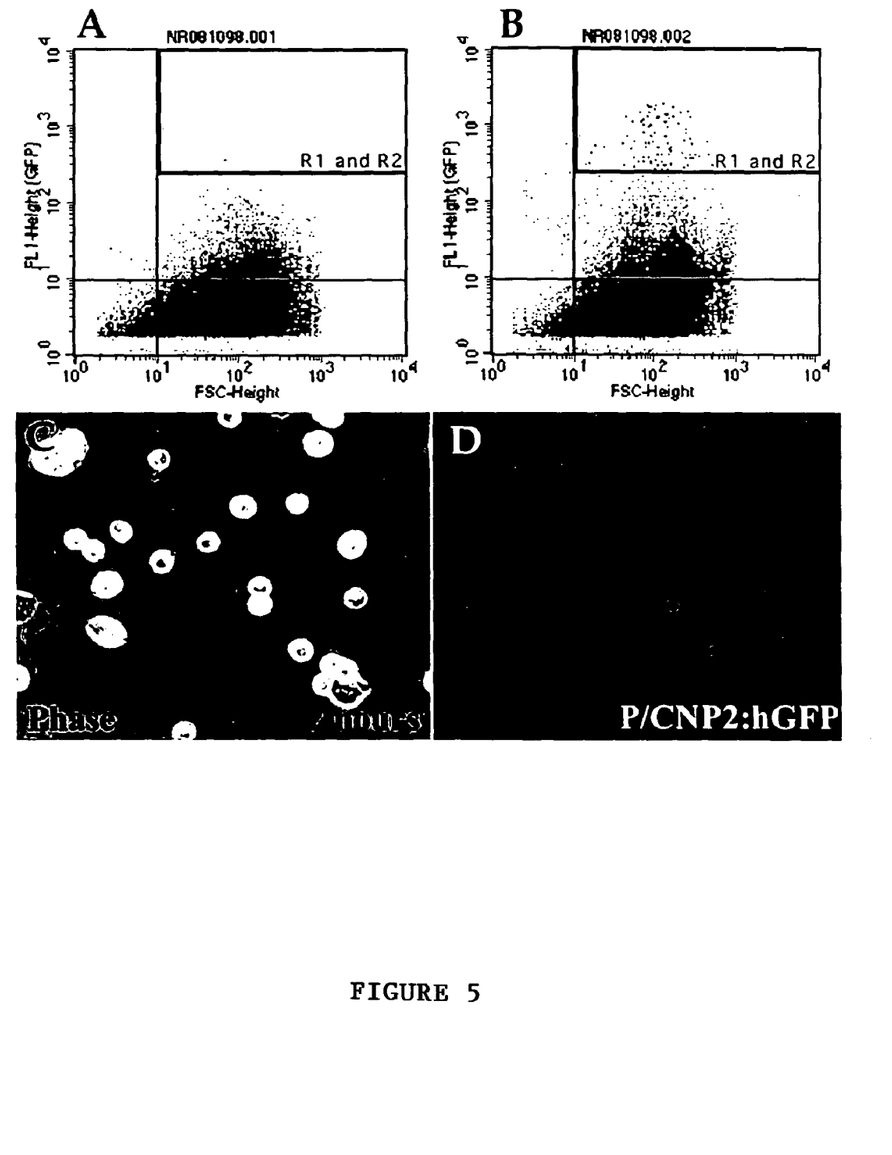
FIGS. 5A-D show that isolation of P/hCNP2:hGFP$^+$ cells by FACS.

Using sorting criteria intended for cell-type purification, the P/hCNP2-driven GFP$^+$ cells were then enriched and cultured separately (FIG. 4). Immediately after FACS, P/hCNP2:hGFP-separated cells largely expressed A2B5-IR. Furthermore, the majority of these A2B5$^+$ cells were found to have incorporated BrdU from their culture medium prior to FACS, indicating their mitogenesis in vitro (FIG. 5). Within the week after sorting, and with concurrent transfer to higher serum media, most of the sorted cells developed O4 expression, and lost A2B5-IR.

Figure 6:
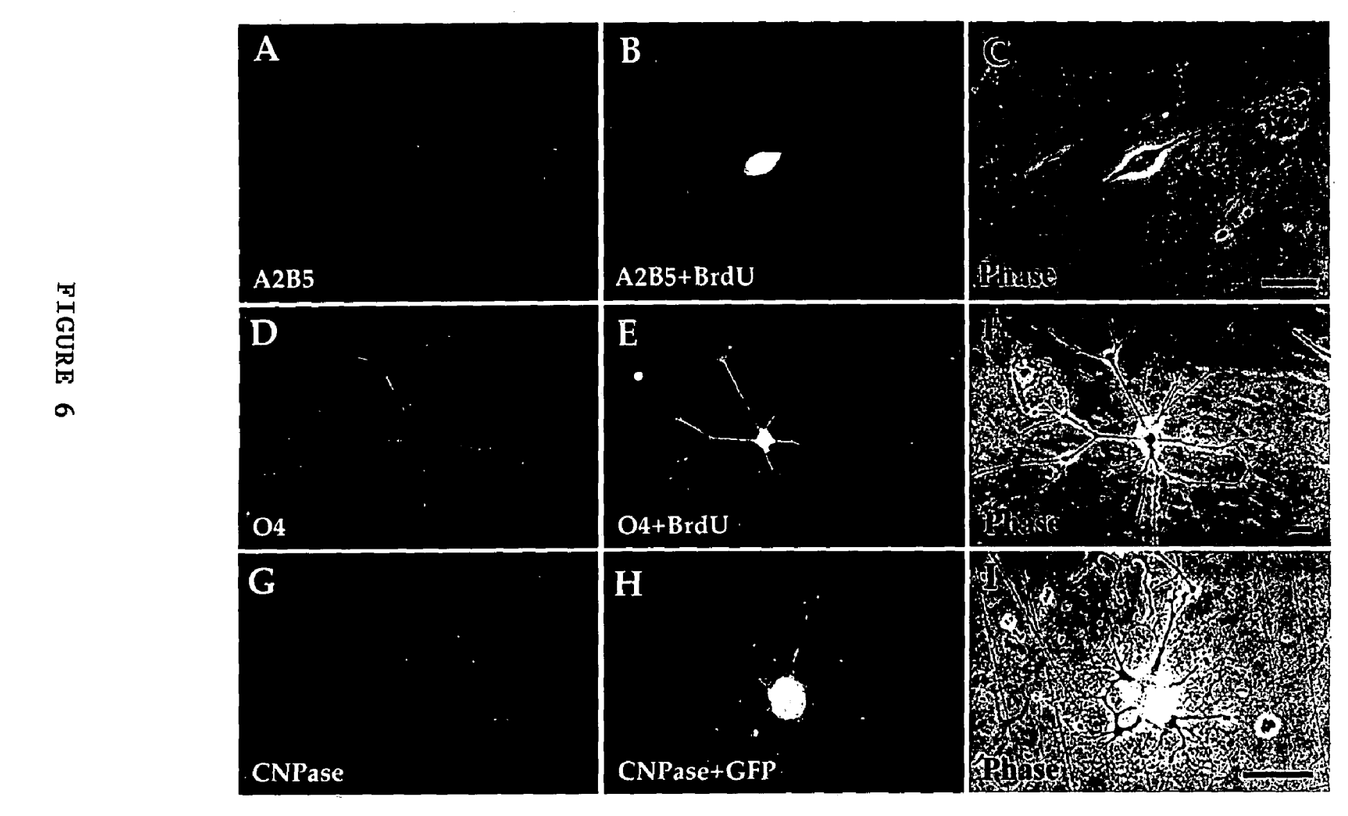
FIGS. 6A-I show P/hCNP2:hGFP-sorted cells divide and express oligodendrocytic markers.

Notably, P/hCNP2:hGFP-separable cells were not rare. Among 7 patients whose white matter dissociates were transfected with P/hCNP2:hGFP, 0.59±0.1% of all subcortical cells expressed the transgene and could be separated on that basis. As a result, typically >2000 pCNP2:hGFP$^+$ cells (2382±944) were obtained from sorts that averaged 352,000 gated cells (FIG. 6). In this regard, net transfection efficiency, determined using P/CMV:hGFP, was 13.5±2.2% (n=3), suggesting that roughly 1 cell in 8 was successfully transfected with the promoter-driven reporter. This in turn suggested that oligodendrocyte progenitor cells comprise at least 4% (0.59%×1/0.135=4.37%) of all cells in the subcortical white matter.

Example 6

Figure 7:
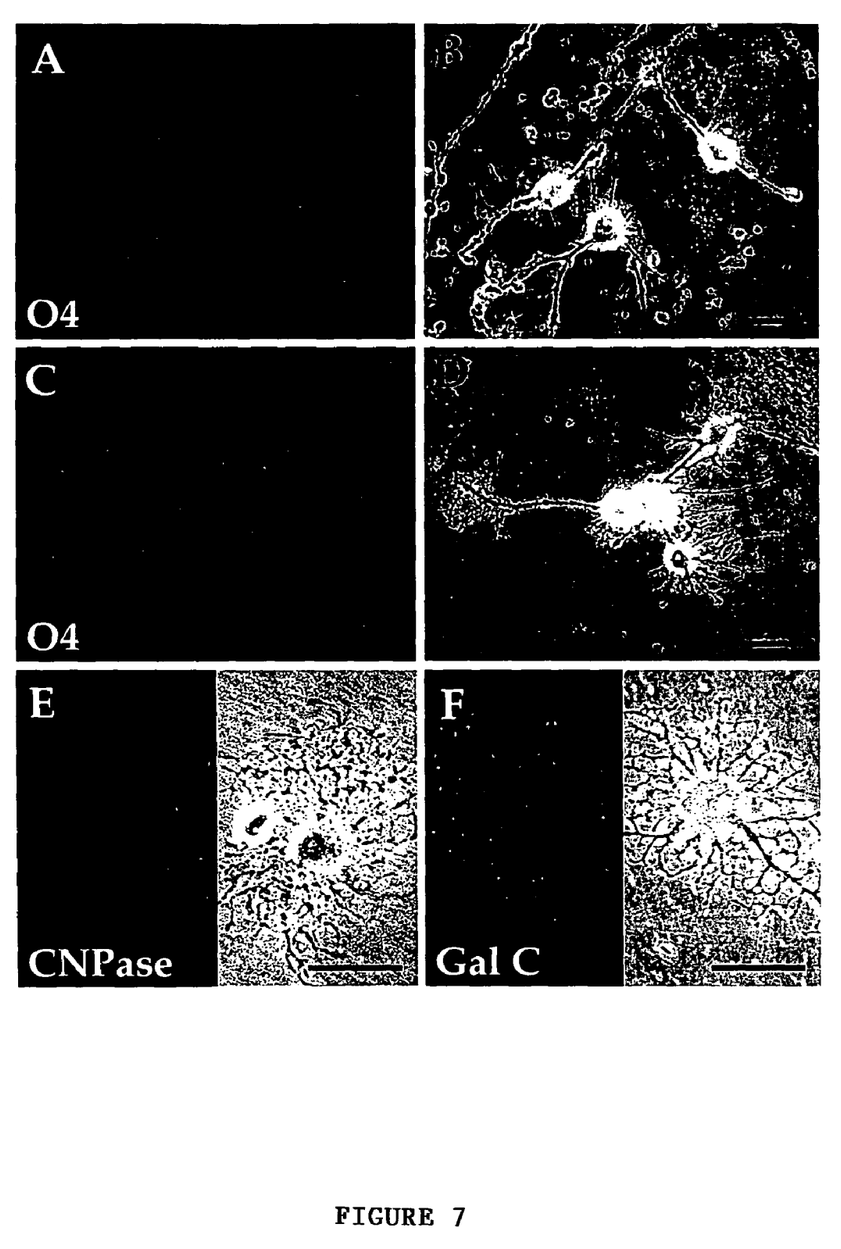
FIGS. 7A-F show FACS-sorted P/hCNP2:hGFP$^+$ cells mature largely as oligodendrocytes.

P/hCNP2:hGFP$^+$-Sorted Cells Matured Largely, but not Exclusively, into Oligodendrocytes The majority of CNP2-sorted cells developed and matured as oligodendrocytes. By 3 weeks after FACS, 74.1±7.7% of these cells expressed oligodendrocytic CNP protein; a matched sample of sorted cells stained after 3 weeks in vitro for O4 yielded 66.3±6.8% O4-IR cells, most of which co-labeled for the more mature marker galactocerebroside (FIG. 7). Nonetheless, concurrent development of non-oligodendrocytic phenotypes was also noted after FACS purification, albeit at lower frequency than oligodendrocytes: Immediately after sorting, 6.5±5.4% of the sorted cells expressed GFAP, and 11.0±4.6% were GFAP$^+$ by 3 weeks in vitro. These were not simply false-positive contaminants, in that most were observed to express P/hCNP2:hGFP fluorescence. No P/hCNP2:hGFP$^+$ neurons, as defined by concurrent TuJ1/βIII-tubulin IR, were observed immediately prior to FACS, but 7.5±4.4% of P/hCNP2:hGFP-sorted cells did mature into TuJ1$^+$ neurons in the week thereafter. These TuJ1$^+$ cells were confirmed visually as expressing P/hCNP2:hGFP. The presence of these sporadic P/hCNP2:hGFP$^+$ neurons and astrocytes after FACS suggests that P/hCNP2-defined progenitors may retain some degree of multilineage potential in vitro.

These data indicate that the adult human subcortex harbors a population of residual, mitotically-competent oligodendrocyte progenitor cells. The cells constitute a discrete population of bipolar blasts, distinct from mature oligodendrocytes. The progenitors were mitotically competent, and as such, distinct from the much larger population of mature, apparently post-mitotic oligodendrocytes. These cells were antigenically immature (A2B5$^+$/O4$^-$) when isolated, but matured (O4$^+$/O1$^+$) over several weeks in culture. Cell-specific targeted reporting, achieved by transfecting the overall white matter pool with plasmids of GFP placed under the control of the early promoter for oligodendrocytic CNP, allowed the live-cell identification of these progenitor cells. This in turn provided a means for their isolation and purification, by fluorescence-activated cell sorting based on P/hCNP2-driven GFP expression.

The Nature of the Adult White Matter Progenitor Pool

Intriguingly, these CNP2-defined oligodendrocytic progenitors were not rare: By the present sorting criteria, they constituted as many as 4% of total white matter cells. The abundance and ubiquity of these cells suggest that they may play an important role in the maintenance and function of the normal adult white matter. In rats, a substantial proportion of the white matter cells population is cycling at any one time. Although this issue has not been well-studied in humans, the presence of such a large progenitor pool in humans suggests that some degree of oligodendrocytic turnover may be occurring in the human subcortical white matter, with the replacement of damaged or dysfunctional postmitotic oligodendrocytes by progenitor-derived replacements. Such speculation notwithstanding, the normative roles of the white matter progenitor pool in both healthy and pathologic brain function remains unclear, and begs further study.

Ontogeny and Lineage of Parenchymal Oligodendrocytic Precursors

Neural precursor cells are widespread in the subependymal zone (SZ) of the forebrain ventricular lining (Goldman, et al., 1983; Goldman, et al., 1992; Kirschenbaum, et al., 1995; Lois, et al., 1993; Luskin, M. B., 1993; and Morshead, et al., 1994). Whether the P/hCNP2:hGFP-defined subcortical precursors described here are co-derived with the SVZ-based progenitor pool is unknown. It is also unclear whether the P/hCNP2-defined precursors constitute committed oligodendrocyte precursors, or whether they are more intrinsically pluripotential, and generate given lineages as a function of the environment to which they are exposed. The latter possibility is suggested by the small proportion of P/hCNP2:hGFP$^+$ cells that were found to be GFAP$^+$ astrocytes upon immunostaining; many of these never developed expression of any oligodendrocytic marker, and appeared instead to be astrocytes. This suggests that the P/hCNP2-defined progenitor pool may constitute a bipotential astrocyte-oligodendrocyte progenitor, which may yield largely oligodendrocytic progeny by virtue of the culture conditions employed. As such, this cell type may well be analogous to its A2B5-defined counterpart in the developing optic nerve (Butt, et al., 1993; Colello, et al., 1995; and Noble, et al., 1992). Whether these cells might also be competent to generate neurons remains unclear. No P/hCNP2:hGFP$^+$ cells were found to express neuronal TuJ1 in unsorted white matter cultures, out of >2000 hGFP$^+$ cells studied. Nonetheless, a small number of TuJ1$^+$ cells were noted to develop in P/hCNP2:hGFP-sorted cultures, and these TuJ1-defined neurons were confirmed as P/hCNP2:hGFP$^+$, rather than nonfluorescent contaminants of the sorts. Thus, with time in vitro, particularly in the mitogenic FGF2/PDGF/NT3 environment provided here, it remains possible that these cells retain or regain a capacity for multi-lineage differentiation, as in development (Davis, et al., 1994 and Williams, et al., 1991). Importantly, only P/hCNP2:hGFP-defined cells were noted to mature as neurons after high-grade enrichment by sorting. Thus, the multilineage potential of these cells might be preferentially exercised after their isolation from other cell types, in low density culture. As such, the relative fidelity to oligodendrocytic phenotype by P/hCNP2:hGFP-defined cells in the initial white matter dissociates, prior to FACS, might reflect an initial restriction of progenitor phenotype by paracrine and/or density-dependent influences in vitro.

Implantation for the Treatment of Demyelinating Diseases

The high-yield acquisition of oligodendrocyte progenitor cells from the adult human brain may allow growth and differentiation requirements specific to these cells to be better defined. Such information may enable their endogenous activation and/or engraftment. The potential use of these cells as substrates for induced remyelination suggests therapeutic strategies appropriate to a variety of white matter diseases. These potential therapeutic targets include ischemic demyelination, as in subcortical lacunar infarction and hypertensive leukoencephalopathy, post-inflammatory demyelinations, such as radiation necrosis and remitted multiple sclerosis, as well as the degenerative and metabolic leukodystrophies.

Taken together, these observations suggest that oligodendrocyte progenitors persist in relative abundance in the adult human white matter. P/hCNP2:hGFP-based FACS permits their viable harvest, in sufficient numbers and purity to enable their potential use in cell-based therapeutic strategies.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

The following is a list of references cited in this application. All of these citations are hereby incorporated by reference.

Alouani et al., *Hum Gene Ther* 3:487-499 (1992).
Andersen et al., *Eur J Cell Bio* 62:324-332 (1993).
Armstrong, R. C., et al., *J Neurosci* 12:1538-1547 (1992).
Arnold, D., et al., *Proc Natl Acad Sci USA* 91:9970-9974 (1994).
Barami, K., et al., *Neuron* 13:567-582 (1994).
Barami, K., et al., *J Neurobiol* 28:82-101 (1995).
Birse, S., et al., *J Comp Neurol* 194:291-301 (1980).
Butt, et al., *J. Comp. Neurol.* 338:141-58 (1993).
Cambi and Kamholz, *Neurochem Res* 19:1055-1060 (1994).
Chalepakis et al., *DNA Cell Biol* 13:891-900 (1994).
Chalfie, M., et al., *Science* 263:802-805 (1994).
Cheng, L., et al., *Nature Biotech* 14:606-609 (1996).
Chin et al., *J Biol Chem* 269:18507-18513 (1994).
Ching et al., *J Biol Chem* 266:19459-19468 (1991).
Collelo, et al., *J. Neurosci.* 15:7665-72 (1995).
Davis, A. A., et al., *Nature* 372:263-266 (1994).
Douglas, et al., *Ann. Human Genetics* 56:243-54 (1992).
Douglas and Thompson, *Biochem Soc. Trans.* 21:295-97 (1993)
Drago, J., et al., *Proc Natl Acad Sci USA* 88:2199-2203 (1991).
Gage, F., et al., *Ann Rev Neurosci* 18:159-192 (1995a).
Gage, F., et al., *Proc Natl Acad Sci USA* 92:11879-11883 (1995b).
Gensert, J. M., et al., *Glia* 17:39-51 (1996).
Gensert, J. M., et al., *Neuron* 19:197-203 (1997).
Gloster, A., et al., *J Neurosci* 14:7319-7330 (1994).
Goldman and Luskin, *Trends in Neurosci.* 21(3): 107-14 (1998).
Goldman, *J. Neurobiol.* 36: 267-86 (1998).
Goldman, et al., *J. Neurobiol.* 30(4): 505-20 (1996).
Goldman, S., *J. Neurosci* 10:2931-2939 (1990).
Goldman, S., *The Neuroscientist* 1:338-350 (1995).
Goldman, S., In: *Isolation, characterization and utilization of CNS stem cells*. F. Gage, Y. Christen, eds., Foundation IPSEN Symposia. Springer-Verland, Berlin, p. 43-65 (1997).
Goldman, S., et al., *Glia* 8:150-160 (1993).
Goldman, S., and Kirschenbaum, B., *Soc Neurosci Abstr* 317.7 (1995).
Goldman, S., and Nedergaard, M., *Dev Brain Res* 68:217-223 (1992).
Goldman, S., and Nottebohm, F., *Proc Natl Acad Sci USA* 80:2390-2394 (1983).
Goldman, S., et al., *J Cereb Blood Flow Metab* 9:471-477 (1989).
Goldman, S., et al., *Molec Cell Neurosci* 7:29-45 (1996).
Goldman, S., et al., *J Neuroscience* 12:2532-2541 (1992).
Gravel, M., et al., *J Neurosci Res* 53:393-404 (1998).
Gravel, M., et al., *Mol. Cell. Neurosci.* 7:453-66 (1996).
Grever, et al., *J. Neurosci. Res.* 47:332-40 (1997).
Gritti, A., et al., *J Neurosci* 16:1091-1100 (1996).
Heim, R., and Tsien, R., *Current biology* 6:178-183 (1996).
Hidalgo, A., et al., *J Neurobiol* 27:470-487 (1995).

Holst et al., *J Biol Chem* 269:22245-22252 (1994).
Kaplan, M., and Hinds, J., *Science* 197:1092-1094 (1977).
Karpov et al., *Biol Cell* 76:43-48 (1992).
Kilpatrick, T., and Bartlett, P., *J Neurosci* 15:3563-3661 (1995).
Kirschenbaum, B., et al., *Cerebral Cortex* 4:576-589 (1994).
Kirschenbaum, B., and Goldman, S., *Soc Neurosci Abstr* 317.8 (1995b).
Kirschenbaum, B., and Goldman, S., *Proc Natl Acad Sci USA* 92:210-214 (1995a).
Koh, J., et al., *Science* 268:573-575 (1995).
Korr, H., *Adv Anat Embryol Cell Biol* 61:1-72 (1980).
Krebs et al., *J Virol* 69:2434-2442 (1995).
Kuhn, et al., *J. Neurosci.* 17(15):5820-29 (1997).
Le Van That et al., *Mol Brain Res* 17:227-238 (1993).
Levy, A., et al., *J Neurosci Res* 43:719-725 (1996a).
Levy, J., et al., *Nature Biotechnol* 14:610-614 (1996b).
Liu and Fischer, *Gene* 171:307-308 (1996).
Lo, D., et al., *Neuron* 13:1263-1268 (1994).
Lois, C., and Alvarez-Buylla, A., *Proc Natl Acad Sci USA* 90:2074-2077 (1993).
Luskin, et al., *Molec. & Cell. Neurosci.* 8:351-66 (1997).
Luskin, *Neuron* 11:173-89 (1993).
Marusich, M., and Weston, J., *J Dev Biol* 149:295-306 (1992).
Marusich, M., et al., *J Neurobiol* 25:143-155 (1994).
Menezes, et al., *J. Neurosci.* 14(9):5399-416 (1994).
Mercer et al., *Neuron* 7:703-716 (1991).
Miller, F., et al., *J Cell Biol* 105:3065-3073 (1987).
Miller, F., et al., *J Neurosci* 9:1452-1463 (1989).
Monoh, et al., *Gene* 129:297-301 (1993).
Morshead, C., et al., *Neuron* 13:1071-1082 (1994).
Morshead, C., and van der Kooy, D., *J Neurosci* 12:249-256 (1992).
Nedergaard, M., et al., *J Neurosci* 11:2489-2497 (1991).
Noble, et al., *Semin. Cell Biol.* 3:413-22 (1992).
O'Neill, R., et al., *J Neurosci Res* 50:248-257 (1997).
Palmer, T., et al., *Mol Cell Neurosci* 6:474-486 (1995).
Peyron, et al., *J. Neurosci. Res.* 50:190-201 (1997)
Pincus, D., et al., *Ann Neurology* 40:550 (1996).
Pincus et al., *Neurosurgery* 42:858-68 (1998a).
Pincus, et al., *Ann Neurol.* 43:576-85 (1998b).
Rasika, S., et al., *Proc Natl Acad Sci USA* 91:7854-7858 (1994).
Reynolds, B., and Weiss, S., *Science* 255:1707-1710 (1992).
Richards, L., et al., *Proc Natl Acad Sci USA* 89:8591-8595 (1992).
Sambrook et al., *Molecular Cloning: A Laboratory Manual*, 2d Edition, Cold Spring Harbor Laboratory Press, Cold Spring Harbor, N.Y. (1989).
Scherer et al., *Neuron* 12:1363-1375 (1994).
Scolding, N. J., et al., *Neuroreport* 6:441-445 (1995).
Shah, N., et al., *Cell* 85:331-343 (1996).
Shahar, A., In: *Methods in Neurosci*, vol. 2.: *Cell Culture*, M. Conn, ed., Academic Press, San Diego, p. 195-209 (1990).
Starr et al., *Brain Res* 638:211-220 (1994).
Sturrock, R., *Adv Cell Neurobiol*, vol. 3, Academic Press, New York, p. 1-33 (1982).
Szabo, A., et al., *Cell* 67:325-333 (1991).
Takebayashi et al., *J Biol Chem* 270:1342-1349 (1995).
Tsukada, et al., *Myelin: Biology and Chemistry* (ed. R. Martenson) pp. 449-480 (1992).
Vescovi, A., et al., *Neuron* 11:951-966 (1993).
Vogel, et al., *Glial* 1:184-81 (1988).
Wang, S., et al., *Nature Biotechnology* 16:196-201 (1998).
Wang, et al., *Ann. Neurol.* 44:438 (1998).
Williams, B. P., et al., *Neuron* 7:685-693 (1991).
Wrabetz et al., *J Neurosci Res* 36:455-471 (1993).
Yu, et al. *Neuron* 12:1353-62 (1994).

What is claimed is:

1. An enriched or purified preparation of human mitotic oligodendrocyte progenitor cells, wherein the majority of cells in the enriched or purified preparation differentiate into O4 positive oligodendrocytes, when cultured in PDGF, FGF2, and NT3, and further develop into galactocerebroside positive oligodendrocytes in the presence of 5% FBS/IGF-1, the mitotic oligodendrocyte progenitor cells are from a postnatal human, and a human cyclic nucleotide phosphodiesterase gene P2 promoter is transcriptionally active in the oligodendrocyte progenitor cells.

2. An enriched or purified preparation of human mitotic oligodendrocyte progenitor cells, wherein the majority of cells in the enriched or purified preparation differentiate into O4 positive oligodendrocytes, when cultured in PDGF, FGF2, and NT3, and further develop into galactocerebroside positive oligodendrocytes in the presence of 5% FBS/IGF-1, the mitotic oligodendroctye progenitor cells are from an adult human, and a human cyclic nucleotide phosphodiesterase gene P2 promoter is transcriptionally active in the oligodendrocyte progenitor cells.

3. An enriched or purified preparation of human mitotic oligodendrocyte progenitor cells, wherein the majority of cells in the enriched or purified preparation differentiate into O4 positive oligodendrocytes, when cultured in PDGF, FGF2, and NT3, and further develop into galactocerebroside positive oligodendrocytes in the presence of 5% FBS/IGF-1, the oligodendrocyte progenitor cells express A2B5 antigen and do not express O4 antigen.

4. An enriched or purified preparation of human mitotic oligodendrocyte progenitor cells, wherein the majority of cells in the enriched or purified preparation differentiate into O4 positive oligodendrocytes, when cultured in PDGF, FGF2, and NT3, and further develop into galactocerebroside positive oligodendrocytes in the presence of 5% FBS/IGF-1, the mitotic oligodendrocyte progenitor cells are from a fetal human and a human cyclic nucleotide phosphodiesterase gene P2 promoter is transcriptionally active in the oligodendrocyte progenitor cells.

5. The enriched or purified preparation of claim 1, wherein the oligodendrocyte progenitor cells do not express GFAP antigen.

6. The enriched or purified preparation of claim 2, wherein the oligodendrocyte progenitor cells do not express GFAP antigen.

7. The enriched or purified preparation of claim 3, wherein the oligodendrocyte progenitor cells do not express GFAP antigen.

8. The enriched or purified preparation of claim 4, wherein the oligodendrocyte progenitor cells do not express GFAP antigen.

9. The enriched or purified preparation of claim 1, wherein the oligodendrocyte progenitor cells do not express βIII tubulin antigen.

10. The enriched or purified preparation of claim 2, wherein the oligodendrocyte progenitor cells do not express βIII tubulin antigen.

11. The enriched or purified preparation of claim 3, wherein the oligodendrocyte progenitor cells do not express βIII tubulin antigen.

12. The enriched or purified preparation of claim 4, wherein the oligodendrocyte progenitor cells do not express βIII tubulin antigen.

13. The enriched or purified preparation of claim 3, wherein the oligodendrocyte progenitor cells are from an adult human.

14. The enriched or purified preparation of claim 3, wherein the oligodendrocyte progenitor cells are from a fetal human.

15. The enriched or purified preparation of claim 3, wherein a human cyclic nucleotide phosphodiesterase gene P2 promoter is transcriptionally active in the oligodendrocyte progenitor cells.

16. The enriched or purified preparation of claim 1, wherein 66.3±6.8% of cells in the enriched or purified preparation mature into O4-1R oligodendrocytes when cultured in the presence of 5% FBS/IGF-1.

17. The enriched or purified preparation of claim 2, wherein 66.3±6.8% of cells in the enriched or purified preparation mature into O4-IR oligodendrocytes when cultured in the presence of 5% FBS/IGF-1.

18. The enriched or purified preparation of claim 3, wherein 66.3±6.8% of cells in the enriched or purified preparation mature into O4-IR oligodendrocytes when cultured in the presence of 5% FBS/IGF-1.

* * * * *